United States Patent [19]

Cahiez et al.

[11] Patent Number: 4,962,215

[45] Date of Patent: Oct. 9, 1990

[54] PROCESS OF PREPARATION OF ENOLIC COMPOUNDS AND NEW PRODUCTS OBTAINED

[75] Inventors: Gérard Cahiez, Bruno Figadere; Pierre Tozzolino, Serres-Morlaas, both of France

[73] Assignee: Societe Nationale Elf Aquitaine, France

[21] Appl. No.: 285,532

[22] Filed: Dec. 16, 1988

[30] Foreign Application Priority Data

Dec. 2, 1988 [FR] France .................................. 88 15806

[51] Int. Cl.$^5$ .............................................. C07F 13/00
[52] U.S. Cl. ...................................................... 556/45

[58] Field of Search ................................. 552/45; 556/7

[56] References Cited

U.S. PATENT DOCUMENTS

| | | | |
|---|---|---|---|
| 3,594,216 | 7/1971 | Charles et al. | 556/45 X |
| 4,336,148 | 6/1982 | Wirther et al. | 556/45 X |
| 4,497,743 | 2/1985 | Brisset et al. | 556/45 X |

Primary Examiner—Paul F. Shaver
Attorney, Agent, or Firm—Ostrolenk, Faber, Gerb & Soffen

[57] ABSTRACT

Enolic derivatives of a ketone are prepared by contacting the ketone with a mixed organo-manganous compound.

19 Claims, No Drawings

PROCESS OF PREPARATION OF ENOLIC COMPOUNDS AND NEW PRODUCTS OBTAINED

The invention relates to a process for the preparation of certain enolic compounds and, more particularly, manganous enolates which have proved very useful for various subsequent syntheses. It allows this preparation under good economic conditions and, moreover, with an excellent regioselectivity. The invention also comprises the manganous enolates produced by this process, which constitute new chemical compounds.

Due to their utility as intermediates for various chemical reactions, enolates have been studied and utilised widely. For example, FLEMING et coll. ("Synthesis" 1976, 736, and "Chem. Soc. Rev." 1981, 10,83) have cited their use in the synthesis of numerous natural products. They serve inter alia for the preparation of various esters, ketones and aldehydes useful in perfumery and as primary materials for the production of medicaments or insecticides. There are numerous processes for the preparation of enolates; thus ethers of silyl enols and esters of enols have been obtained by treating, for example with trimethylchlorosilane, or with a carboxylic acid anhydride, the product obtained by the reaction of a ketone with NaH in dimethoxyethane or with Li diisopropylamide in the same solvent. Ethers of silyl enols have also been obtained by treating a ketone with a tertiary amine or with 1,4-diazo-bicyclo(2,2,2)octane in the presence of tri-methylchlorosilane, in dimethylformamide, etc. In certain cases, the yields are good, but with asymmetric ketones, quantities of the product corresponding to the thermodynamic enolate form, while the yields leave much to be desired in the rare procedures which lead to a majority of the product corresponding to the kinetic enolate. Also, most prior techniques are delicate operations, particularly because large numbers of them require, in order to obtain the kinetic enolate, excesses of the reactants (up to 2.5 times) and very low temperatures, of the order of −80° C. Thus, despite the existing prior art, there is a need for a practical process which will permit the economic preparation of enolates and their derivatives.

The present invention responds to this need, rendering possible the easy preparation of enolic compounds, starting from ketones, at temperatures slightly above or below 0° C., with high or very high yields; the process allows the exclusive or substantially exclusive production of the kinetic enolate, when the starting ketone is asymmetric. The enolates obtained according to the invention store well at temperatures generally slightly above or below 0° C.

The process according to the invention, which comprises the reaction of a ketone with an organo-metallic compound, is characterised in that this compound is a mixed organo-manganous compound leading to the formation of an enolate of Mn.

This process is especially unexpected, as current organo-metallic compounds, particularly those of Mg or of Li, give, under the same conditions, the product resulting from a 1,2-addition to the carbonyl of the ketone, that is a tertiary alcoholate and not the enolate of the ketone. Thus for example with RMgX:

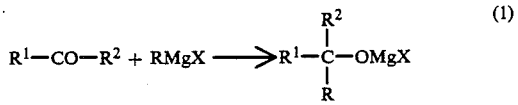

which, by hydrolysis, leads to

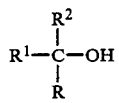

In contrast, according to the invention, a mixed organo manganous compound R-MnX is reacted with the ketone, giving both the manganous derivative of the tertiary alcohol

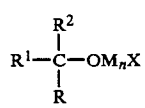

in a fashion analogous to the reaction (1) above and an enolate formed by the process:

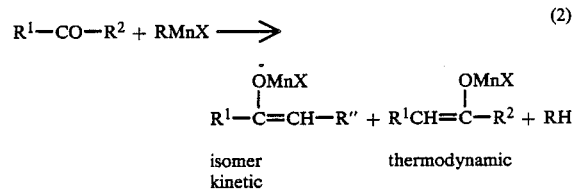

comprising the removal of a proton with consecutive formation of RH.

The difference between the thermodynamic and kinetic isomers appears solely with asymmetric ketones and it will thus be seen better in the example of the reaction of R-MnCl with propylethylketone CH$_3$CH$_2$CH$_2$—CO—CH$_2$CH$_3$, which leads to three manganous compositions:

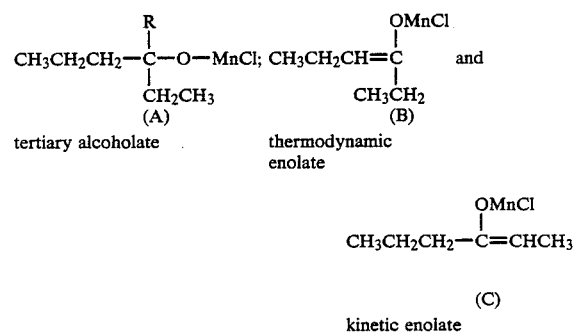

The proportions of the compounds of the types A, B and C vary depending upon the nature of the ketone treated, that of the solvent, the temperature, the nature of R, etc. While it may be useful in a certain industry to obtain the three compounds simultaneously, it is more interesting to produce one or other of the isomers, either kinetic or thermodynamic, to a maximum, the kinetic isomer being more difficult to obtain by the prior technique. Moreover this is precisely the unexpectedly result which the present invention allows to obtain economically.

The preparation of mixed enolates of manganese according to the invention comprises the contact of a ketone and a mixed organo-manganous compound in an appropriate solvent, maintained at a temperature from −50° to +50° C., for half to 20 hours in the absence of air. The temperatures most often utilised are from 10° to +20° C., the time of the reaction most usually being from 1 to 3 hours. Stoichiometric proportions of the reactants are most useful in general, that is to say it is desirable to employ 1 mole of the mixed organo-manganous compound RMnX with 1 mole of the ketone $R^1$—CO—$R^2$, or 2 moles of RMnX per mole of a diketone.

The manganese enolate formed (B and/or C shown above) can be recovered from the reaction medium by evaporation in the absence of air and humidity from the solvent or by any other known means, in order to be converted into the desired derivative. However, in most current uses, it is simple to treat this enolate in situ, in its original solvent, if required after adding another solvent and/or modifying the temperature, before introducing a suitable new reactant. Thus it is possible to acylate, silylate, alkylate, halogenate, hydroxyalkylate, etc. this product in its reaction medium, by the addition of an acid anhydride or chloride, a trialkysilyl halide, an allyl halide or an alkyl halide, a halogen, an aldehyde, or even water etc. The manganese is eliminated in the course of these reactions and there are obtained the enol esters concerned or the β-diketones, silylated derivatives or the corresponding ketones which may be alkylated, allylated or halogenated etc. Thus, use of the mixed enolate of allows the preparation of various products resulting from modification of the initial ketone.

The process of the invention is applicable to various ketones. Among suitable monoketones are the linear aliphatic, such as

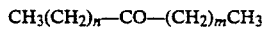

where the numbers n and m are the same or different and range from 0 to 17. On the other hand, in one or each of their chains $(CH_2)_n$ and $(CH_2)_m$, there can be a double or triple bond and/or an alkyl or aryl substituent. Similar ketones carry in place of the one or two terminal CH3 groups a secondary or tertiary group namely

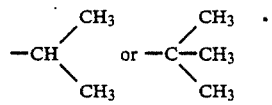

Ketones can also be utilised in which one or the two chains $CH_3(CH_2)_n$ or $CH_3(CH_2)_m$ are replaced by a phenyl, tolyl, xylyl, naphthyl, cyclopentyl, cyclohexyl or cyclohexenyl ring which can carry one or more alkyl substituents. The ketones employed can carry functional groups (halogens, alkoxy, thioalkoxy etc). By way of non limitative examples, the invention can be carried out by starting with ketones such as diethylketone, dipropylketone, di-isopropylketone, ethylpropylketone, ethylhexylketone, ethylphenylketone, but y lcyclopentanone, methylcyclohexanone, hexylheptylketone, butyldodecylketone, acetophenone, etc.

The chemical composition of the mixed organo-manganous compound, RMnX, has considerable importance in carrying out the invention. In particular, the yield of a desired enolate depends considerably on the nature of the groups R and X, the appropriate choice of which allows remarkable results to be obtained.

In a general manner, R can be any hydrocarbon group, aliphatic, cycloaliphatic or aryl, or an amino group. It is preferable however for it not to carry too many side chains capable of exerting steric hindrance. Particularly suitable as R are alkyl chains, preferably methyl, alkenyl or alkynyl having $C_1$ to $C_{20}$, preferably having $C_1$ to $C_{12}$, particularly groups which do not contain eliminatable β H atoms. R can also be a cyclopentyl or cyclohexyl which can carry one or more $C_1$ to $C_{12}$ alkyl substituents. Particularly suitable for R are aryl rings, in particular phenyl or naphthyl, possibly carrying 1 to 3 $C_1$ to $C_{12}$ alkyl substituents; thus phenyl, tolyl, xylyl, mesityl, mono-, di- or tri-ethylphenyl, dipropylphenyl etc. form interesting R groups. A methyl or phenyl at R has the advantage of allowing the preparation in very good yields at moderate temperatures, particularly between 0° and 30° C., while with heavier alkyls than methyl, for example butyl, it is necessary to work at around −50° C. The nature of the group X in the organo-manganous compound RMnX is of great importance. In principle, X can be any element, radical or group capable to serving as a ligand for the manganese complex. It can particularly be a halogen, an anion for example a compound of S, P, B, C or Si, an oxy- or thiohydrocardon group, an amino group etc. Thus, for example X is Cl, Br or I, $CF_3SO_2$, R'COO, $BF_4$, -OR' or —SR' (R' being an alkyl or aryl), —NR$_2$' or —NR'R" (R',R" being hydrocarbon groups) etc.

According to a particular feature of the invention, X can be a basic group if it is desired to produce the enolate as far as possible. It is thus possible to have as a major part or exclusively the kinetic enolate starting from the asymmetric ketone. These reactions also present the particularity of leading principally to the configuration Z for the enolate products (ratio E/Z=25:75 to 0:100), which in general is very favourable for industrial applications.

As regards basic X groups, particularly suitable are substituted amino groups, of the type —NR$_2$' or—NR'R", or NR'R", where the hydrocarbon radicals R' and R" can be aliphatic, especially $C_1$ to $C_{18}$, cycloaliphatic and/or aryl, particularly phenyl, which advantageously can be substituted, preferably with 1 to 3 $C_1$ to $C_{12}$ alkyls.

It is preferable that at least one of R' and R" should be an aryl, because this leads to much better yields than are given by alkyls alone. Phenylmethylamides of the type

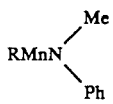

can be stored for several months at ambient temperature.

It can be seen from the foregoing that the invention offers various possibilities for obtaining the desired results with a given ketone; the person skilled in the art can adopt appropriate R and X groups, guided by the specific examples which are found below in the present description.

A factor which equally influences the results of enolisation according to the invention is the nature of the solvent. The principal solvents utilisable are ethers, particularly diethyl oxide, pyrane, 1,2-dimethoxyethane and especially tetrahydrofuran;, use can also be made however of dimethylsulphoxide or sulpholane, other solvents being known to the person skilled in the art which can take into account the yields and regioselectivity which can vary with the nature of the solvent.

The highly recommendable use of organo-manganous compounds of the type RMn—NR'R" can be realised in the form of a variant providing a certain economy. It has been established that in place of preliminary preparation of the compound RMn—NR'R", for use in the reaction (2) in place of RMnX, use can be made for this purpose of a less efficacious organo-manganous compound, for example RMnCl, but adding to the reaction medium an amine HNR'R", capable if required of forming the compound R—Mn—NR'R" in situ. This leads to the same excellent results as this compound gives when it has been prepared and is introduced in advance into the reaction medium. But there is more; it has been unexpectedly established that by putting only a part of the amine stoichiometrically required, for example 1/5th of this quantity, a yield is obtained which is much better than with R—Mn—Cl alone.

This leads to a variant characterised in that the enolisation is effected by the reaction of a ketone which any organo-manganous compound, particularly R—Mn—X, where X is a halogen, within a solvent, the medium also including an amine HN-R'R" in a catalytic quantity.

In fact, as can be seen, according to Examples 42 to 46, the quantity of amine added can range between about 5 and 50% of the stoichiometric proportion with respect to the RMnX present.

The invention is illustrated by the non-limitative examples which follow.

In most of the examples, preparation of a mixed enolate of Mn is carried out first, starting from a ketone; then an acylating agent is added to the reaction medium, generally propionic anhydride $(CH_3CH_2CO)_2O$, in order to form the propionic ester corresponding to the enol; after separation of it, the yield of the ketone and the E/Z ratio are determined; in the case of asymmetric ketones, the percentage of the kinetic isomer (regioselectivity) is also evaluated.

$$R^1-C\!\!=\!\!CH-R''$$
$$\phantom{R^1-C\!\!=\!\!}|$$
$$\phantom{R^1-}O-\!\!\underset{\underset{\displaystyle O}{\|}}{C}\!\!-CH_2CH_3$$

The mode of operation consists of using a solution of 100 mmoles of the organo-manganous compound RMnX in 200 ml of THF or ether between $-10°$ and $0°$ C., to which is added 100 mmoles of ketone, while agitating. The mixture is then allowed to stand at the ambient temperature.

After 2 hours it is cooled to $-10°$ C., then 200 mmoles of the acylating agent (propionic anhydride) is added and, with agitation, the temperature is allowed to rise to the ambient.

After two hours, the mixture is subjected to hydrolysis at $-10°$ C. with 160 ml of water. It is then filtered or acidified (with HCl, $H_2SO_4$) to give dissolution of the salts. The decanted aqueous phase is subjected to extraction three times with 100 ml of ether.

The reunited organic phases are dried over $MgSO_4$, the solvent being evaporated under vacuum; the residue, that is to say the products of these operations, is isolated and purified by distillation.

EXAMPLES 1 to 9

Enolisation of dipropylketone $C_3H_7$—CO—$C_3H_7$ ($Pr_2CO$) with various butyl-MnX organo-manganous compounds (Bu MnX) at $-50°$ C. Then acylation by means of propionic anhydride $(C_2H_5CO)_2O$ and measurement of the products obtained.

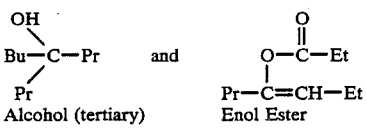

Alcohol (tertiary)     Enol Ester

The results are summarized in Table I below.

TABLE I

| Example | BuMnX | Solvent | tertiary alcohol | enol ester | ketone recovered |
|---|---|---|---|---|---|
| | | | Yields % | | |
| 1 | BuMnCl | THF | 75 | 5–20 | 0 |
| 2 | BuMnOBu | " | 8 | 34 | 55 |
| 3 | BuMnN(iPr)$_2$ | " | 28 | 47 | 0 |
| 4 | BuMnNPhMe | " | 1–2 | 92 | 0 |
| 5 | BuMnNEt$_2$ | Et$_2$O | 21 | 68 | 3 |
| 6 | BuMnN(iPr)$_2$ | " | 23 | 76 | 0 |
| 7 | BuMnN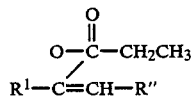 | " | 11 | 40 | 45 |
| 8 | BuMnNPhMe | " | 8 | 90 | 0 |
| 9 | PhMeNMnBr | " | 0 | 70 | 30 |

It can be confirmed that the better yields of the enol ester are obtained with BuMnX where X is an amino group, in particular N methyl phenyl amino.

EXAMPLES 10 to 15

Enolisation of dipropylketone as in Examples 1–9, but with RMnX where the X is the group

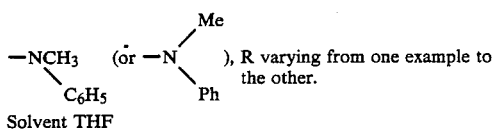

Solvent THF

TABLE II

| Ex. no. | R | Temperature | Yield % |
|---|---|---|---|
| 10 | Bu | 0° C. | 77 |
| 11 | " | −50° C. | 92 |
| 12 | Me | 0° C. | 93 |
| 13 | Ph | " | 95 |
| 14 | Me$_2$C=CH | " | 92 |
| 15 | PrC≡C— | " | 80 |

Examples 12 to 14 indicate an optimum yield in enol when operating at 10° C., R being a phenyl or methyl. Examples 10 and 11 show that it is possible to improve the yield by lowering the enolisation temperature when R is an alkyl group heavier than methyl.

EXAMPLES 16 to 21

Enolisations (solvent=THF) similar to those of the preceding Examples, but at 20° C., with the organomanganous compound PhMnX, where X is an amino group changing from one example to the other.

| Ex no | X | Yield % |
|---|---|---|
| 16 | −N(Me)(Ph) | 95 |
| 17 | −N(Ph)(CH₂CH(C₂H₅)(C₂H₅)) | 94 |
| 18 | −N(Ph)(Ph) | 92 |
| 19 | −N(Bu)(Bu) | 40 |
| 20 | −N(CH(CH₃)(CH₃))(CH(CH₃)(CH₃)) | 40 |
| 21 | −N morpholino | 23 |

This confirms that the presence of at least one aryl group on the nitrogen contributes to a marked increase in the yield of the enol ester.

EXAMPLES 22 to 28

Enolisation in ether according to the technique of examples 1 to 9 at −50° C., but starting from various ketones

TABLE III

| | | | Yields % | |
|---|---|---|---|---|
| Ex no | Ketone | RMnX | tertiary alcohol | enol ester |
| 22 | iPr₂CO | BuMnN(iPr)₂ | 7 | 65 |
| 23 | PhCOPr | " | 21 | 71 |
| 24 | cyclohexanone | " | 10 | 60 |
| 25 | Pr₂CO | " | 23 | 76 |
| 26 | " | BuMnEt₂ | 21 | 68 |
| 27 | iPrCOBu | " | 3 | 87 |
| 28 | iBuCOHept | " | 6 | 86 |

The differences of behavior of the various ketones are here more easy to observe than they were in the optimum conditions (Example 4 or 16) because the percentage of tertiary alcohol formed in Examples 4 or 16 is too low to allow the differences in behavior to be appreciated. EXAMPLES 29 to 41

Enolisation at −50° C. according to the mode of operation of the preceding Examples, starting from various ketones with various mixed organo-manganous compounds, either in ether or tetrahydrofuran; various anhydrides are then employed to acylate the enolate formed; as well as the yield of enol ester corresponding to the kinetic enolate, the stereochemical cis/trans configuration of this ester (E/Z ratio) is determined.

TABLE IV

| Ex. no. | Ketone | BuMnX | Solvent | (RCO)₂O | Kinetic Yield (%) | E/Z | Thermo Yield |
|---|---|---|---|---|---|---|---|
| 29 | (CH₃)₂CH—CO(CH₂)₃—CH₃ | BuMnNEt₂ | Et₂O | (EtCO)₂O | 87 | 0/100 | 0 |
| 30 | (CH₃)₂CH—CH₂—CO(CH₂)₆CH₃ | " | " | " | 86 | 10/90 | 2 |
| 31 | 2-methylcyclohexanone | BuMnNPhMe | " | " | 96 | — | 0 |
| 32 | EtCOEt | " | " | " | 88 | 20/80 | — |
| 33 | " | " | THF | " | 92 | 0/100 | — |
| 34 | PrCOPr | " | Et₂O | " | 90 | 20/80 | — |
| 35 | " | " | THF | " | 91 | 0/100 | — |
| 36 | " | " | Et₂O | (iPrCO)₂O | 83 | 25/75 | — |
| 37 | " | " | " | (BuCO)₂O | 88 | 20/80 | — |
| 38 | PrCOPr | BuMnN(iPr)₂ | " | (EtCO)₂O | 76 | 20/80 | — |
| 39 | iPrCOiPr | " | " | " | 65 | — | — |
| 40 | PhCOPr | BuMnNPhMe | " | " | 80 | 0/100 | — |
| 41 | cyclohexanone | BuMnN(iPr)₂ | " | " | 60 | — | — |

It is surprising to see that the E/Z ratio is always between 25/75 and 0/100 (or 1/3 to 0), although in the prior art with yields of 78 to 100% there are E/Z values of 96/5 and 99.5/0.5 (R. E. IRELAND et coll. J. Amer. Chem. Soc. 1976, 2868; E. I. NAKAMURA et coll. Tetrahedron Letters 1978, 2079). The two authors appear agreed, through the use of 2,2,6,6-tetramethyl-piperidine of Li (LiTMP) for enolisation that E/Z ratios can be obtained of 16/84 and 5/95, but then the yields do not exceed 70% (E. I. NAKAMURA cited above and Z. A. FATAFTAH et coll. G. Am. Chem. Soc. 1980, 3959).

EXAMPLES 42–46

Enolisation according to a variant utilising an amine as catalyst.

The main lines of the mode of operation are those of Examples 1 to 9 with, as the organomanganous compound, phenyl manganese chloride

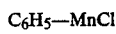

n mmoles of which are reacted with 100 mmoles of dipropylketone $C_3H_7$—CO—$C_3H_7$, in 200 ml of THF, at 0° C. for 30 minutes, a quantity of the amine being previously added to the medium

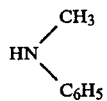

indicated in the results Table V below. As for the preceding Examples, the reaction medium containing the mixed enolate of Mn formed is treated with propionic anhydride and the yield of the enol ester obtained is then determined.

The results table which follows indicates the numbers of moles of amine and of Ph—MnCl utilised per 100 moles of ketone.

TABLE V

| Example no | n PhMnCl | mmoles Amine | Yield % |
|---|---|---|---|
| 42 | 107.5 | 7.5 or 6.9% | 72 |
| 43 | 120 | 20 or 16.7% | 85–88 |
| 44 | 150 | 50 or 33.3% | 87 |
| 45 | 200 | 100 or 50.0% | 95 |
| 46 | 100 | 0 or 0 | 64 |

EXAMPLE 47

Enolisation according to Example 43 within a special solvent formed from 3 volumes of THF with 1 volume of sulpholane

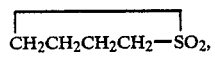

tetramethylene-sulphone). With 20% amine, a yield of 94% is obtained.

EXAMPLES 48 to 54

Use of mixed manganous enolates in alkylation. In the preceding examples, the solution of the Mn enolate obtained according to the invention was treated with an acid anhydride, which led to an enol ester. Here the subsequent treatment is effected by the addition to the solution in THF of an organic halide $R^3X$. 2 moles of $R^3X$ are thus added to 1 mole of Mn enolate; operation was at ambient temperature for 2 hours, after which the product formed was isolated. Then a ketone was obtained homologous to that, $R^1COR^2$, which had served for the formation of the manganous enolate, according to the reactions:

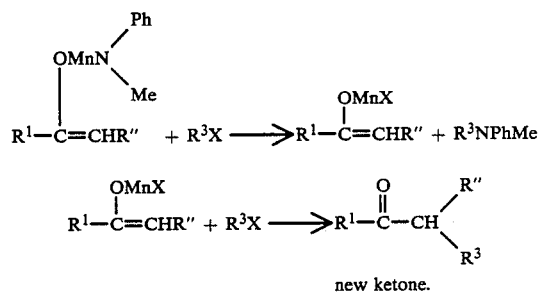

new ketone.

The Table VI below indicates the yields of the new ketone obtained with respect to that which had served for preparation of the organo manganous compound.

TABLE VI

| Ex no | Initial Ketone | Solvent | $R^3X$ | Yield % in new ketone |
|---|---|---|---|---|
| 48 | Pr—CO—Pr | THF | ICH3 | 76 |
| 49 | " | " | IC4H9 | 55 |
| 50 | " | THF + DMSO | " | 62 |
| 51 | " | THF | PhCH2Br | 75 |
| 52 | Pr—CO—Pr | THF/DMSO | Allyl bromide (CH2=CH—CH2Br) | 91 |
| 53 | Pr—CO—Bu | THF/ sulpholane | Allyl bromide (CH2=CH—CH2Br) | 98 |
| 54 | BU-CO-Bu | THF | BrCH2COOEt | 88 |

EXAMPLES 35–63

Use of mixed manganous enolates in the preparation of silylated enol ethers. Operation at $-50°$ C.

In a fashion analogous to the foregoing examples, the prepared the manganous enolate solution was treated with 1.3 mole of trimethylsilyl chloride $(CH_3)_3SiCl$ per —MnX group present in the form of

(thermodynamic isomer)    (kinetic)

After 2 hours at the ambient temperature, the two isomers corresponding to the silylated ether were obtained, when the starting ketone which has served for production of the manganous enolate is asymmetric. Thus:

(thermodynamic)    (kinetic)

Starting from various ketones and various organomanganous compounds, silylated enol ethers were obtained with the yields and in the proportions of isomers which follow.

TABLE VII

| Ex. n° | Initial Ketone | Bu-MnX | Ratio of kinetic thermo | Over-all % Yield | Z/E Ratio (Kinetic isomer) |
|---|---|---|---|---|---|
| 55 | PrCOPr | Bu-MnNPhMe | — | 88 | 100/0 |
| 56 | iPrCOBu | " | 100/0 | 70 | 100/0 |
| 57 | PhCOPr | " | — | 89 | 100/0 |
| 58 | iBuCOHept | " | 100/0 | 93 | 98/2 |
| 59 | PhCH₂COPr | " | 100/0 | 90 | 100/0 |
| 60 | BuCOEt | " | 66/34 | 90 | — |
| 61 | " | Bu-MnN(iPr)₂ | 53/47 | 90 | — |
| 62 | " | Bu-MnNPh₂ | 55/45 | 79 | — |
| 63 | HeptCOEt | Bu-MnNPhMe | 58/42 | 89 | — |

Note: Z/E ratios were found here which were even more remarkable than in Table IV (see page 15, lines 1-12).

EXAMPLES 64 to 68

Preparation and silylation of manganous enolates between −10° and 0° C. in THF. The organo-manganous compound utilised was

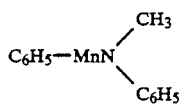

Silylation was effected with 1.2 equivalents of $(CH_3)_3SiCl$ with respect to the ketone. Depending upon the ketone employed, the yields of silylated ether are:

| Example no | Ketone | Yield % |
|---|---|---|
| 64 | Pr—CO—Pr | 80 |
| 65 | $C_6H_{13}-\underset{\underset{O}{\|}}{C}-CH_2CH_2CH\begin{smallmatrix}CH_3\\CH_3\end{smallmatrix}$ | 82 |
| 66 | $C_6H_5-\underset{\underset{O}{\|}}{C}-CH_2CH_2CH_3$ | 86 |
| 67 | $C_2H_5-\underset{\underset{O}{\|}}{C}-C_7H_{15}$ | 86 |
| 68 | cyclohexanone with CH₃ substituent | 88 |

We claim:

1. Process of preparation of an enolic derivative from a ketone by contact thereof with an organo metallic compound, characterised in that the organo metallic compound is a mixed organo-manganous compound and the derivative formed is an Mn enolate.

2. Process according to claim 1, characterised in that in the mixed organo-manganous compound R—Mn—X, R designates a hydrocarbon group or an amino group and X designates a ligand for the manganese complex.

3. Process according to claim 2, characterised in that R is a $C_1$ to $C_{20}$ alkyl chain, $C_2$ to $C_{20}$ alkenyl or alkynyl, or a cycloalkyl, which can carry one or more $C_1$ to $C_{12}$ alkyl substituents.

4. Process according to claim 3, characterised in that R is methyl.

5. Process according to claim 2, characterised in that R is aryl, which can carry 1 to 3 $C_1$ to $C_{12}$ alkyl substituents.

6. Process according to claim 1 characterised in that X is —NR'R", where R' and R" are the same or different hydrocarbon groups.

7. Process according to claim 6, characterised in that X is a —NR'R" group where R' is a $C_1$ to $C_6$ alkyl, R" is an aryl or both R' and R" are aryls.

8. Process according to claim 1 in which the reactants are prepared in a solvent.

9. Process according to claim 1, characterised in that the reaction takes place between −50° and +50° C.

10. Process according to claim 1 characterised in that, in RMnX, X is a halogen or an anion and an amine HNR'R" is added to the solution of the reactants in the amount of 5 to 50 moles per 100 miles of RMnX present.

11. Process according to claim 10, characterised in that the reaction is carried out in a mixture of THF and sulpholane.

12. New chemical product constituted by a mixed Mn enolate.

13. Product according to claim 12, characterised by the formulae

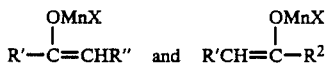

where $R^1$, $R^2$, R' and R" are independently selected from the group consisting of $C_1$ to $C_{17}$ aliphatic hydrocarbon groups and aryl, and X designates a ligand for the manganous complex.

14. Product according to claim 13, characterised in that X is —NR'R" where R' and R" are the same or different hydrocarbon groups.

15. Process according to claim 3 characterised in that R is $C_1$ to $C_{12}$ alkyl, $C_2$ to $C_{12}$ alkenyl or alkynyl, cyclopentyl or cyclohexyl.

16. Process according to claim 5 in which R is phenyl or naphthyl.

17. Process according to claim 6 in which R' and R" are $C_1$ to $C_{18}$ aliphatic or aryl groups which may be substituted with 1 to 3 $C_1$ to $C_6$ alkyls.

18. Process according to claim 8 in which the solvent is an ether and the reaction takes place between −10° and +20° C.

19. Process according to claim 2 in which X is selected from the group consisting of Cl, Br, I, $CF_3SO_2$, R'COO, $BF_4$, OR, and SR', where R' is alkyl or aryl.

* * * * *